United States Patent [19]

Kleiner

[11] Patent Number: 6,077,968
[45] Date of Patent: *Jun. 20, 2000

[54] PROCESS FOR THE PREPARATION OF ALKYL ARYLPHOSPHINITES

[75] Inventor: Hans-Jerg Kleiner, Kronberg, Germany

[73] Assignee: Celanese GmbH, Germany

[ * ] Notice: This patent is subject to a terminal disclaimer.

[21] Appl. No.: 08/900,596

[22] Filed: Jul. 25, 1997

Related U.S. Application Data

[63] Continuation of application No. 08/593,667, Jan. 29, 1996, Pat. No. 5,705,669.

[30] Foreign Application Priority Data

Jan. 31, 1995 [DE] Germany .................. 195 02 913
Jan. 31, 1995 [DE] Germany .................. 195 02 911

[51] Int. Cl.$^7$ ........................................ C07F 9/32
[52] U.S. Cl. ............................................. 558/96
[58] Field of Search ........................ 558/96

[56] References Cited

U.S. PATENT DOCUMENTS 2,903,475  9/1959  Harowitz .................. 558/96

*Primary Examiner*—Michael G. Ambrose
*Attorney, Agent, or Firm*—Connolly, Bove, Lodge &Hutz LLP

[57] ABSTRACT

A process for the preparation of alkyl arylphosphinites of the formula (I)

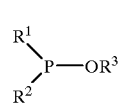

(I)

in which
$R^1$ is $(C_1-C_{16})$-alkyl, cyclohexyl, cyclopentyl, aryl which can also be substituted by halogen, $(C_1-C_6)$-alkoxy groups
$R^2$ is aryl which can also be substituted by halogen, $(C_1-C_6)$-alkyl, $(C_1-C_6)$-alkoxy groups, where $R^1$ and $R^2$ together with the phosphorous atom can also form a ring and
$R^3$ is $(C_1-C_4)$-alkyl,
which comprises reacting halo(aryl)phosphines of the formula (II)

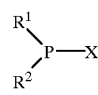

(II)

in which $R^1$, $R^2$ have the meaning given above and X is halogen, with ammonia-containing alcohols of the formula (III)

$R^3OH$   (III)

in which $R^3$ has the meaning given above.

10 Claims, No Drawings

PROCESS FOR THE PREPARATION OF ALKYL ARYLPHOSPHINITES

CROSS REFERENCE TO RELATED APPLICATION

This is a continuation of application Ser. No. 08/593,667, filed Jan. 29, 1996, now U.S. Pat. No. 5,705,669.

The invention relates to a process for the preparation of alkyl arylphosphinites.

Arylphosphinous esters, in particular diphenyl phosphinous esters are of considerable interest as intermediates for the preparation of phosphine oxides. These serve, for example, as photoinitiators (EP-B 0 007 508). Arylphosphinous esters are prepared by reacting halo(aryl)phosphines with alcohols in the presence of tertiary amines (eg. EP-B 0 229 686). Adding additional at least molar amounts of ammonia is said to favor the reaction (U.S. Pat. No. 3,057,904). In addition, a process for the preparation of phosphonous esters and phosphinous esters is known, in which the hydrogen halide (in particular hydrogen chloride) produced is neutralized only with ammonia (U.S. Pat. No. 2,903,475). This process is particularly interesting for obvious reasons, since the economic advantages with high yields are readily recognizable. The process is carried out in such a manner that the halophosphine is added to the alcohol at about 20° C. and ammonia is simultaneously added in a controlled manner such that the hydrogen halide formed is immediately neutralized by ammonia. However, the yields in this process are unsatisfactory for phosphinous esters. Thus, in the reaction of chloro(diethyl)phosphine with butanol, butyl diethylphosphinite is only obtained in a yield of 21.7% of theory. Furthermore, this process requires high control expenditure to control pH and rate of addition of the ammonia.

There was therefore the need to improve this ammonia process in such a way that the desired products are formed in high yield and high purity without high expenditure on equipment.

This object is achieved by a process for the preparation of alkyl arylphosphinites of the formula (I)

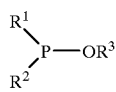
(I)

in which
R$^1$ is (C$_1$–C$_6$)-alkyl, cyclohexyl, cyclopentyl, aryl which can also be substituted by halogen, (C$_1$–C$_6$)-alkoxy groups
R$^2$ is aryl which can also be substituted by halogen, (C$_1$–C$_6$)-alkyl, (C$_1$–C$_6$)-alkoxy groups, where R$^1$ and R$^2$ together with the phosphorous atom can also form a ring and
R$^3$ is (C$_1$–C$_4$)-alkyl, which comprises reacting halo(aryl)phosphines of the formula (II)

(II)

in which R$^1$, R$^2$ have the meaning given above and X is halogen, with ammonia-containing alcohols of the formula (III)

 (III)

in which R$^3$ has the meaning given above.

The process is important, eg., for the conversion of compounds of the formula (II) in which aryl is phenyl or substituted phenyl and X is chlorine. of particular interest is the reaction for converting methyl(phenyl)chlorophosphine, methyl(o-phenyl)chloro-phosphine, methyl(p-tolyl)chlorophosphine, methyl(p-methoxyphenyl)chlorophosphine, hexyl(phenyl)chloro-phosphine, octyl (phenyl) chlorophosphine, diphenyl(chloro)phosphine, bis(p-fluorophenyl)chloro-phosphine, 2,3-difluorophenyl (phenyl)chlorophosphine.

Alcohols which may be used are, eg., methanol, ethanol, isopropanol or n-butanol. Ethanol, in particular, is preferred. The alcohols must be as free from water as possible. They must be used in excess. This excess, in the ratio of halophosphine: alcohol, is 1:3.5 to 1:20, preferably 1:4.5 to 1:15 mol. In addition, inert solvents such as toluene or chlorobenzene can be used.

It has proved to be useful in many cases to carry out the process in such a way that the halophosphines are added in solutions of ammonia in the alcohols, in the presence or absence of inert solvents. The addition is advantageously performed at −25 to +5° C., in particular −18 to −5° C., preferably −15 to −10° C. The ammonia and halophosphine are used in a molar ratio of 1:1 to 2:1, in particular 1.1:1 to 1.8:1. After addition of the chlorophosphine, the mixture is further stirred at room temperature. As an additional measure, the application of vacuum or passing inert gases such as nitrogen through the mixture can be expedient in order to expel ammonia.

However, heating the mixture for several hours, for example at temperatures of 60 to 120° C., during which ammonia escapes, has proved to be a particularly expedient variant of the workup. After about 5 to 20 hours, the escape of ammonia gas is ended. After post-treatment has ended, ammonium chloride is separated at room temperature and the filtrate is worked up by distillation in a conventional manner.

Surprisingly, the desired end products are obtained in high yields, although the formation of phosphinous amides of the type R$_2$P—NH$_2$ would be expected (Houben-Weyl, Methoden der organischen Chemie [Methods in organic chemistry], Georg Thieme Verlag Stuttgart, Vol. XII/1, page 213, 1963; U.S. Pat. No. 2,903,475).

When post-treatment is carried out at 60 to 120° C., it must be described as surprising that no isomerization reaction could be observed, since it is known that crude phosphinous esters are thermally unstable and readily isomerize at elevated temperature to phosphine oxides (Houben-Weyl, Methoden der organischen Chemie [Methods in organic chemistry], Georg Thieme Verlag Stuttgart, Vol. XII/1, page 150, 1963).

A further advantageous process variant is to add the halo(aryl)phosphines to the alcohols at temperatures of −25 to +5° C. and then to introduce ammonia at these temperatures.

This process variant is advantageously carried out in such a manner that the halophosphine, optionally mixed with the solvent, is added to the alcohol under nitrogen atmosphere at −20 to 0° C., in particular −18 to −5° C., preferably −15 to −10° C. and the hydrogen halide formed is then reacted with ammonia.

Good results are achieved, eg., if the addition of the chlorophosphine takes about one to two hours and the reaction of the ammonia is likewise completed in one to two hours. The ammonia is expediently used in excess in order to ensure that the reaction material remains in the alkaline region. After the reaction is complete, the mixture is expediently further stirred at room temperature and then filtered off by suction from the ammonium chloride formed. The filtrate is worked up by distillation in a conventional manner. The process can also be carried out continuously. For certain applications, the phosphinous esters prepared by the process are produced in such a pure form even as crude products that purification by distillation can be dispensed with.

In this process variant it is particularly surprising that a plurality of side reactions described in the literature (U.S. Pat. No. 2,903,475) such as $R_2POR'+HCl \rightarrow R_2POH+R'Cl$ $2R_2PCl+NH_3 \rightarrow R_2P-NH_2$ do not occur. Furthermore, the following side reaction was also to be expected:

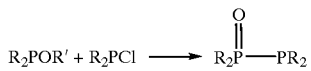

EXAMPLE 1

330 g (7.17 mol) of absolute ethanol are cooled to −15° C. under a nitrogen atmosphere. 26.5 g (1.56 mol) of ammonia gas are introduced thereto at this temperature with constant stirring. 200 g (0.907 mol) of chloro(diphenyl)-phosphine are then added dropwise at this temperature. The mixture is then allowed to come to room temperature with stirring and is then kept under reflux for 11 hours until virtually no more ammonia gas escapes. The mixture is then cooled, filtered by suction, washed with ethanol and dried. 48 g of crude ammonium chloride are obtained. The filtrate is freed from ethanol and any ammonia present in vacuo. The remaining residue is freed from a slight salt precipitate by filtration through a glass frit. 170 g of ethyl diphenylphosphinite are then obtained by thin film distillation at a bath temperature of 160 to 175° C. and a pressure of 0.5 mbar. This corresponds to a yield of 82% of theory.

EXAMPLE 2

330 g (7.17 mol) of absolute ethanol are cooled to −15° C. under a nitrogen atmosphere. 18 g (1.06 mol) of ammonia gas are then introduced at this temperature. 200 g (0.907 mol) of chloro(diphenyl)phosphine are then added dropwise at this temperature in one hour. The mixture is then allowed to come to room temperature with stirring and is stirred for a further 3.5 hours. The mixture is then cooled, filtered by suction and washed with ethanol. The filtrate is freed from ethanol and any ammonia present in vacuo. The remaining residue is freed from a slight precipitate by filtration through a glass frit. 172 g of ethyl diphenylphosphinite are then obtained by thin film distillation at a bath temperature of 140° C. and 0.3 mbar. This corresponds to a yield of 83% of theory.

If the process is carried out in such a manner that the mixture is brought to room temperature after completion of the dropwise addition of chloro(diphenyl)phosphine, then kept under reflux for 12 hours and then worked up as above after cooling, 195 g of ethyl diphenylphosphinite are obtained. This corresponds to a yield of 94% of theory.

EXAMPLE 3

90 g (1.96 mol) of absolute ethanol are cooled to −15° C. under a nitrogen atmosphere. 4.95 g (0.29 mol) of ammonia are then introduced at this temperature with constant stirring. 64.1 g (0.25 mol) of bis-(4-fluorophenyl)-chlorophosphine are then added dropwise in the course of 50 minutes at this temperature. The mixture is then allowed to come to room temperature under stirring and is kept under reflux for 12 hours. The mixture is then cooled, filtered by suction, washed with ethanol and dried. 13 g of ammonium chloride are obtained. The filtrate is freed from ethanol in vacuo and the residue is distilled at 0.45 mbar at an overhead temperature of 102° C. 55 g of ethyl bis-(4-fluorophenyl) phosphinite are obtained. This corresponds to a yield of 83% of theory.

EXAMPLE 4

135 g (2.94 mol) of absolute ethanol are cooled to −15° C. under a nitrogen atmosphere. 7.4 g (0.435 mol) of ammonia are then introduced at this temperature with constant stirring. 86 g (0.376 mol) of chloro-(n-hexyl)phenyl-phosphine are then added dropwise at this temperature in 40 minutes, then the mixture is allowed to come to room temperature with stirring, is filtered by suction and washed with ethanol. The filtrate is freed from ethanol and any ammonia present in vacuo. The remaining residue is distilled. 71 g of ethyl n-hexyl(phenyl)phosphinite are obtained at 1.1 mbar and an overhead temperature of 110° C. This corresponds to a yield of 79% of theory.

EXAMPLE 5

50 g (1.09 mol) of absolute ethanol are cooled to −15° C. under a nitrogen atmosphere. 3 g (1.76 mol) of ammonia gas are then introduced at this temperature with constant stirring. 26 g (1.39 mol) of phenyl(isopropyl)chloro-phosphine are then added dropwise at this temperature in 30 minutes. The mixture is then stirred for a further 30 minutes at this temperature and then refluxed for a further 12 hours. The mixture is then cooled, filtered by suction and rinsed out with ethanol. The filtrate is freed from ethanol in vacuo and the remaining residue is distilled. 23 g of ethyl isopropyl (phenyl)phosphinite are obtained at 0.07 mbar and an overhead temperature of 50° C. This corresponds to a yield of 85% of theory.

EXAMPLE 6

1000 g (21.7 mol) of absolute ethanol are cooled to −15° C. with stirring under a nitrogen atmosphere. 660 g (3.0 mol) of chloro(diphenyl)phosphine are then added dropwise at this temperature with vigorous stirring in the course of one hour and twenty minutes. 76 g (4.47 mol) of ammonia gas are then introduced at this temperature with further vigorous stirring. The mixture is then allowed to come to room temperature with stirring and is stirred for a further six hours. The mixture is then filtered with suction and rinsed out with ethanol. The filtrate is freed from ethanol and excess ammonia in vacuo. A crude product is obtained which is freed from a slight salt precipitate by filtration through a glass frit. 635 g of ethyl diphenylphosphinite are obtained by thin film distillation at a bath temperature of 160 to 175° C. and a pressure of about 0.5 mbar. This corresponds to a yield of 92% of theory.

EXAMPLE 7

915 g (15.25 mol) of n-propanol are cooled to −15° C. with stirring under a nitrogen atmosphere. 330 g (1.5 mol) of chloro(diphenyl)phosphine are then added dropwise at this temperature with vigorous stirring in one hour and 15 minutes. 38 g (2.24 mol) of ammonia gas are then introduced at this temperature with further vigorous stirring. The mixture is then stirred for a further ten hours without cooling. After filtering off the ammonium chloride by suction, the filtrate is freed from propanol and excess ammonia in vacuo. The remaining residue is distilled (boiling point 122° C. at 0.4 mbar). 230 g of propyl diphenylphosphinite are obtained. This corresponds to a yield of 63% of theory.

EXAMPLE 8

210 g (6.56 mol) of absolute ethanol are cooled to −15° C. under a nitrogen atmosphere. 200 g (0.907 mol) of chloro(diphenyl)phosphine are then added dropwise at this temperature with vigorous stirring. 18 g (1.06 mol) of ammonia gas are then introduced. The mixture is then stirred without cooling for 10 hours and filtered by suction. The filtrate is freed from methanol and excess ammonia in vacuo. The residue is filtered by suction through a glass frit. 143 g of crude methyl diphenylphosphinite are obtained. This corresponds to a yield of 73% of theory.

EXAMPLE 9

87 g (1.90 mol) of absolute ethanol are cooled to −15° C. under a nitrogen atmosphere. 67 g (0.26 mol) of bis-(4-fluorophenyl)chlorophosphine are then added dropwise at this temperature in 50 minutes with vigorous stirring. 5.2 g (0.31 mol) of ammonia gas are then introduced at this temperature. The mixture is then further stirred until room temperature is reached and stirred for a further 16 hours. The mixture is then filtered by suction and rinsed out with ethanol. The filtrate is freed from ethanol and excess ammonia in vacuo. The remaining residue is distilled at 0.45 mbar at an overhead temperature of 102° C. 58 g of ethyl bis-(4-fluorophenyl)-phosphinite are obtained. This corresponds to a yield of 84% of theory.

What is claimed is:

1. A process for the preparation of alkyl arylphosphinites of the formula (I):

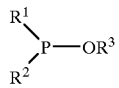
(I)

in which $R^1$ is $(C_1–C_{16})$-alkyl, cyclohexyl, cyclopentyl, aryl which can also be substituted by halogen, $(C_1–C_6)$-alkoxy groups, $R^2$ is aryl which can also be substituted by halogen, $(C_1–C_6)$-alkyl, $(C_1–C_6)$-alkoxy groups, where $R^1$ and $R^2$ together with the phosphorous atom can also form a ring, and $R^3$ is $(C_1–C_4)$-alkyl, which comprises reacting a halo (aryl)phosphine of the formula (II):

(II)

in which $R^1$, $R^2$ have the meaning given above and X is halogen, by adding a neutralizing agent consisting essentially of ammonia to a solution of the phosphine and an alcohol of the formula (III):

 (III)

in which $R^3$ has the meaning given above, wherein the alcohol is present in excess based on the phosphine and wherein essentially all of the phosphine is present in the solution prior to the addition of the neutralizing agent.

2. The process as claimed in claim 1, wherein aryl is phenyl or substituted phenyl and X is chlorine.

3. The process as claimed in claim 1, wherein formula (II) is methyl (phenyl) chlorophosphine, methyl (p-tolyl) chlorophosphine, methyl (p-methoxy-phenyl) chlorophosphine, hexyl (phenyl) chloro-phosphine, octyl (phenyl) chlorophosphine, diphenyl (chloro) phosphine, bis (p-fluoro-phenyl) chlorophosphine or 2,3-difluoro-phenyl (phenyl) chlorophosphine.

4. The process as claimed in claim 1, wherein formula (III) is ethanol.

5. The process as claimed in claim 1, wherein the ratio of halophosphine:alcohol is 1:3.5 to 1:20.

6. The process as claimed in claim 1, wherein the ratio of halophosphine:alcohol is 1:4.5 to 1:15.

7. The process as claimed in claim 1, wherein the process is carried out at a temperature of −25 to +5° C.

8. The process as claimed in claim 1, wherein the alcohol used is anhydrous.

9. The process as claimed in claim 1, wherein ammonia and halophosphine are used in the molar ratio of 1:1 to 2:1.

10. The process as claimed in claim 1, wherein the yield is at least 63% of theory.

* * * * *